(12) United States Patent
Mahadevan-Jansen et al.

(10) Patent No.: US 6,921,413 B2
(45) Date of Patent: Jul. 26, 2005

(54) METHODS AND DEVICES FOR OPTICAL STIMULATION OF NEURAL TISSUES (75) Inventors: Anita Mahadevan-Jansen, Nashville, TN (US); Karthikeyan Mariappan, Mountain View, CA (US); Peter Konrad, Old Hickory, TN (US)

(73) Assignee: Vanderbilt University, Nashville, TN (US)

( * ) Notice: Subject to any disclaimer, the term of this patent is extended or adjusted under 35 U.S.C. 154(b) by 163 days.

(21) Appl. No.: 10/333,700
(22) PCT Filed: Aug. 15, 2001
(86) PCT No.: PCT/US01/25501
§ 371 (c)(1),
(2), (4) Date: Jan. 23, 2003
(87) PCT Pub. No.: WO02/13906
PCT Pub. Date: Feb. 21, 2002

(65) Prior Publication Data
US 2003/0208245 A1 Nov. 6, 2003

Related U.S. Application Data
(60) Provisional application No. 60/225,690, filed on Aug. 16, 2000.

(51) Int. Cl.[7] .............................................. A61N 5/067
(52) U.S. Cl. ........................................ 607/89; 128/898
(58) Field of Search ............................... 607/88–93, 48; 128/898

(56) References Cited

U.S. PATENT DOCUMENTS

| 3,900,034 | A | | 8/1975 | Katz et al. ................... 128/395 |
|---|---|---|---|---|
| 4,966,144 | A | * | 10/1990 | Rochkind et al. ............. 607/89 |
| 5,409,482 | A | | 4/1995 | Diamantopoulos ........... 606/13 |
| 5,445,146 | A | * | 8/1995 | Bellinger ...................... 607/89 |
| 5,464,436 | A | | 11/1995 | Smith ........................... 607/89 |
| 5,514,126 | A | | 5/1996 | Prescott ........................ 606/10 |
| 5,616,140 | A | | 4/1997 | Prescott ........................ 606/10 |
| 5,871,522 | A | * | 2/1999 | Sentilles ....................... 607/94 |
| 6,033,431 | A | | 3/2000 | Segal ............................ 607/89 |
| 6,152,882 | A | * | 11/2000 | Prutchi ........................ 600/509 |
| 6,233,480 | B1 | | 5/2001 | Hochman et al. ........... 600/476 |
| 6,494,900 | B1 | * | 12/2002 | Salansky et al. .............. 607/89 |

* cited by examiner

Primary Examiner—Roy D Gibson
Assistant Examiner—Henry M Johnson, III
(74) Attorney, Agent, or Firm—Morris, Manning & Martin; Tim Tingkang Xia, Esq.

(57) ABSTRACT

The present invention provides methods of directly stimulating neural tissue with optical energy. By stimulating neural tissue at wavelengths, laser pulses, and spot sizes disclosed herein, nerve stimulation may be used to uniquely stimulate neural tissue in way not afforded by other means of stimulation. It can allow basic scientists to study the properties of individual neurons or populations of neurons without piercing tissue with fragile microelectrodes. Furthermore, responses of neural tissue can be studied in a pure fashion without contamination by electrical artifact commonly seen with electrical stimulation. With respect to clinical uses, optical stimulation can be used to map function in subsections of peripheral nerves as an aid to operative repair. Finally, stimulation with optical energy does not require physical contact with the nerve which may be an advantage clinically when physical manipulation of neural tissue is not desired.

8 Claims, 9 Drawing Sheets

METHODS AND DEVICES FOR OPTICAL STIMULATION OF NEURAL TISSUES

This application is a 371 of PCT/US01/25501 Aug. 15, 2001 which claims benefit of 60/225,690 Aug. 16, 2001.

TECHNICAL FIELD

The present invention relates generally to the stimulation of neural tissues. More specifically, the present invention concerns a method for stimulating neural tissues by optical irradiation.

BACKGROUND ART

The present invention discloses in vivo methods that are useful, for example, for exciting individual cells without piercing them, for diagnostic applications like peripheral nerve conduction studies, evoking potentials and mapping neurological functions. The method is also useful for removing electrical artifacts that are commonly found when electrical stimulation is used. Finally, the method is useful for stimulating small subunits of nerve fibers.

Various methods may be used to stimulate neural tissue. Several of the traditional methods of stimulation include electrical, mechanical, thermal, and chemical. A neuron will propagate an electrical impulse after applying a stimulus. The most common form of applying such stimulus is to form a transient current or voltage pulse applied through electrodes. Electrical stimulation, as well as mechanical and chemical stimulation, has many limitations. To name a few, stimulation by such methods may result in non-specific stimulation of neurons or damage to neurons. Difficulty exists in recording electrical activity from the neuron due to an electrical artifact created by the stimulus. To stimulate only one or a few neurons, fragile micro-electrodes need to be fashioned and carefully inserted into the tissue to be stimulated. Such techniques do not easily lend themselves to implantable electrodes used for long term stimulation of neural tissue.

Fork was the first to report a direct stimulation of nerve fibers using low-energy laser light (Fork, R., "Laser stimulation of nerve cells in Aplysia", Science, March(5): p. 907–8, 1971.) Laser irradiation at (488 nm, 515 nm, and 1006 nm) was applied to the abdominal ganglion of *Aplysia Californica* that possesses some light sensitive properties. The author observed that the cells fired when the light at 488 nm was turned on in some cases and turned off in others. In another study, bundles of rat nervous fibers were stimulated using a XeCl laser (Allegre, G., S. Avrillier, and D. Albe-Fessard, "Stimulation in the rat of a nerve fiber bundle by a short UV pulse from an excimer laser", Neuroscience Letters, 180(2): p. 261–4, 1994.) When stimulated using a laser pulse transmitted through an optical fiber, a response similar to that obtained with electrical stimulation was observed. A threshold stimulation level of 0.9 J/cm$^2$ was reported for optical stimulation. No other reports by the same authors have been published since. Thus, optical energy can be used to stimulate nerve fibers. Although there is ample evidence that photon energy effects neural tissue in humans and animals, a need remains for a method that can be used to stimulate neural tissue without damaging such tissue or producing artifacts. Furthermore, in order for such an invention to be useful in both research and clinical applications, it should produce activity in neurons by delivery of energy without the addition of potentially toxic dyes or at intensities destructive to the neuron over useful periods of time. Finally, there is a need for a method of precisely stimulating an individual neuron with optical energy without piercing tissue.

One common way of providing light energy for stimulation of neural tissues is by using a laser. Lasers are characterized by their wavelength and energy level. Classically, lasers have been used in biological applications for tissue ablation. However, low power lasers are available for uses other than tissue ablation. The energy required for stimulation large populations of neurons is very small, and the energy required to stimulate an individual neuron is exceedingly small. Manipulation of strength, duration and frequency of stimulation are key parameters that determine whether a neuron will fire. Such parameters are adjustable with pulsed, optical energy and can be adjusted to a range acceptable for stimulation of neural tissue. Additionally, the precision of laser energy delivery can easily provide a novel method of selectively stimulating individual neurons or different nerve fibers within a large population of neurons without the need to pierce tissue.

It is clear that several major drawbacks exist with respect to the current stimulation methods that are available. Thus, a method of optical stimulation for neural tissue is needed.

The present invention provides methods for stimulating neural tissue with optical energy. Although the present invention is not bound by mechanism or theory, it is related to the surprising discovery by the inventors of methods of stimulating neural tissue with optical energy. Stimulation of neural tissue in this regard includes, but is not limited to, generation and propagation of an electrical impulse in one or more neurons after applying an optical stimulus. In addition, there is a unique basic science and clinical need for producing an artifact-free response in neurons that causes no damage to the tissue.

One advantage of the present invention is that the methods of stimulating neural tissue described herein are contemplated to be highly specific to individual nerve fibers As intensity of electrical stimulation increases, progressively greater numbers of neurons are activated. This is a physical property of associated with increasing the electrical field size. Optical energy, however, can be confined to a predetermined, physical "spot" size, which is independent of the energy delivered. This physical property is what allows optical techniques to be unique in stimulation of individual or selected neurons. Another advantage of the present invention is the use of the methods of stimulation of neural tissues in vivo. In vitro methods of stimulation, on the other hand, do not lend themselves to the uses of an in vivo method.

Still another advantage of the present invention is that optical stimulation of neural tissue is not associated with an electrical stimulus artifact. Thus, when optically stimulating individual or multiple neurons stimulated by optical energy, electrical stimulus artifacts are not present.

Still another advantage of this method is that the use of low energy laser stimulation provides precise localization without tissue contact, resulting in high specificity. Such specificity is of use clinically when nerve stimulation is used for diagnostic applications like identification of subsets of peripheral nerve fibers during operative repair of severed nerves. Also, such technology would allow multiple, focused laser stimuli, to be used to provide functional mapping of neural networks and their interconnections. This advantage may also be applied in therapeutic situations such as neural modulation for pain management, control of movement disorders, and seizure reduction.

Additional aspects, embodiments, and elements of the present invention are described below, including the detailed description of the invention, the examples, and the claims. Aspects, embodiments, and elements described herein are not meant to limit the present invention in any way. Further aspects, embodiments, elements and equivalents thereof, will be readily apparent based upon the present disclosure and are considered to be within the spirit and scope of the present invention.

DISCLOSURE OF THE INVENTION

Given the shortcomings of the currently existing methods of stimulation of neural tissue it is critical that effective and practical methods of stimulating neural tissue with optical energy are identified. Although not bound by mechanism or theory, the present invention takes advantage of the discovery by the inventors of methods of using optical energy to stimulate neural tissue. Provided herein are methods for stimulating either neural tissue, or individual neurons, by using optical energy.

Certain utilities of the methods of the present invention include, but are not limited to: stimulating neural tissue, stimulating individual neurons, diagnosing neural damage in humans and animals, and recording responses to neural stimulation not having electrical artifacts.

Definitions

Unless otherwise defined, all technical and scientific terms used herein have the same meaning as commonly understood by one of ordinary skill in the art to which this invention pertains. In the case of conflict, the present document, including definitions will control.

Descriptions of preferred methods are provided herein, but should not be construed to be limiting.

FEL is an abbreviation for free electron laser.

CNAP is an abbreviation for compound nerve action potential.

CMAP is an abbreviation for compound muscle action potential.

As used herein "target neural tissue" is defined as any neural tissue including, but not limited to, the sciatic nerve of the leopard frog (*Rana Pepieis*), the sciatic nerve of mammals, and brain and spinal cord tissue of mammals.

As used herein "electrical impulse" is defined an electrical current applied via electrodes on the nerve to initiate an action potential in the neuron.

As used herein "stimulation effect" is defined as propagation of an electrical signal within neural or muscular tissue As used herein "nerve fiber" is defined as a portion of the neuron, namely the axon, which carries action potentials from one end of the neuron to the other. Many nerve fibers compose a peripheral nerve, such as the sciatic nerve of a leopard frog (*Rana Pepiens*) or a mammal.

As used herein "an area in a range of or a spot size of $d_1$ micrometers to $d_2$ micrometers," where $d_1$, $d_2$ are numbers, is synonymic to "an area with a diameter in a range of from $d_1$ micrometers to $d_2$ micrometers," as known to people who skilled in the art. For example, an area in a range of 50 micrometers to 600 micrometers is synonymic to an area with a diameter in a range of from 50 micrometers to 600 micrometers, corresponding to an area with a size in a range of 1964 micrometers$^2$ to 282,737 micrometers$^2$, estimated by using the formula of Area Size=¼π$^2$.

Northern Leopard Frog (*Rana Pepiens*) Sciatic Nerve Model System

Leopard frogs (*Rana Pepiens*) provide a widely accepted model system for studying the stimulation of a neural tissue. The frog sciatic nerve provides a robust nerve preparation not susceptible to ischemic changes. Additionally, frogs have a neuromuscular innervation similar to mammals, and extensive research has been carried out by the research community on the ability of neurons to conduct an electrical impulse (reviewed by Meyer and Hegmann, *American Journal of Physiology*, 220(5): 1383–7). Finally, leopard frogs (*Rana Pepiens*) provide a model system that is capable of withstanding temperature and humidity variations (Theophilidis and Pavlidou, *Muscle & Nerve*, 16(1):113–114).

Northern leopard frogs (*Rana Pepiens*) of sizes varying from 3–4 inches are selected so that the sciatic nerve may serve as the target neural tissue. The frogs are pithed so as to euthanize the animal. The frog is pithed to make it brain dead, while still maintaining the vital body functions and the nerve conduction. Subsequent to being pithed, the animal is immobilized on a wax bed. The skin covering the hamstring muscle is cut in order to expose the muscle. Subsequently, an incision is made along the length of the hamstring muscle so as to expose the sciatic nerve. The sciatic nerve is freed from the connective tissue that connected it to the surrounding muscle. For experimental purposes, several pairs of electrodes were placed on the nerve. The first pair of electrodes is capable of electrical stimulation, the second pair of electrodes is capable of recording the nerve potentials, and the third pair of electrodes were pierced into the muscle that the sciatic nerve innervates so that muscle potentials may be recorded. Additionally, the sciatic nerve was kept moist at all times by using saline water.

The methods described herein have been used to stimulate a Rat sciatic nerve, as shown in FIGS. 11–14. One of ordinary skill in the art understands the differences in the surgical procedure necessary to expose the Rat sciatic nerve compared to the surgical procedure described above for the frog. The same method of optical stimulation was used for the Rat nerve and frog nerve. Regarding the stimulation of the Rat sciatic nerve, a wavelength of 4.4 micrometers, and energy of 4.7 mJ, a spot size of 619 micrometers, and a pulse frequency of 2 Hz using the FEL were used. Optical stimulation was also tested using an energy of 39 mJ, 1.78 mJ, and 2.39 mJ.

Free Electron Laser

A free electron laser and delivery optics are used to generate and manipulate the optical energy. The optical energy transport system is maintained under rough vacuum. The optical energy is focused on the target neural tissue using focusing lenses (Vi Convex Lenses, f=300 mm) to a spot size of around 400 micrometers.

The response of the sciatic nerve to the optical energy stimulation is sensed using stainless steel needle electrodes that are placed under the sciatic nerve for compound nerve action potential recording. Additionally, the electrical response from the sciatic nerve is monitored by recording electrodes placed in the nerve downstream and innervated hamstring muscle. If the sciatic nerve conducts an electrical impulse, a tiny electrical signal can be detected from the nerve (CNAP) and a much larger electrical signal can be detected from the muscle (CMAP). The signals are recorded using the MP100 system from Biopac Systems (Santa Barbara, Calif.) which is combined electrical stimulation and recording unit. The nerve was electrically stimulated using S44 Grass electrical stimulator from Grass Instruments, Quincy, Mass.

Optical stimulation was performed using laser pulses with energy in the range from 0.2 mJ to 5 mJ with a spot size of 300–600 micrometers (fluence values varied from 0.2 J/cm$^2$ to about 10 J/cm$^2$). The minimum energy and therefore fluence required to stimulate the frog nerve was found to be minimum (0.6 J/cm$^2$) between 4 and 4.5 micrometers. The spot size of the optical energy was determined using the knife-edge method (J. M. Khosrofian and B. A. Garetz, *Applied Optics*, 22(21): 3406–3410, 1983). The laser pulses were focused onto the sciatic nerve using Biconvex Lenses. The laser pulse energy was varied using a polarizer. The information recorded on the MP100 system was displayed using the AcqKnowledge software.

The FEL was selected for use in the initial studies with this method since it has the following advantages. The FEL is tunable in wavelength from 2 to 10 micrometers. Thus, FEL offers the flexibility of providing various wavelengths in the infrared spectrum for use with the method provided herein. Other sources may be used to generate the necessary wavelength. In addition to any source that can generate wavelengths in the infrared portion of the spectrum, sources may include LED and LCD. FEL additionally provides micropulses, each about 1 picosecond in duration and having a repetition rate of about 3 GHz. The envelope of this pulse train forms a macropulse that is about 3–6 microseconds and can be delivered at a rate up to 30 Hz. As mentioned above, optical stimulation of the peripheral nerves employ pulse energies ranging from 0.2 mJ to 5 mJ in a spot size of around 500 micrometers.

Stimulation studies can also be performed using other sources such as a YAG laser for wavelengths in the UV, visible and infrared. Additionally, if it is desired to use a wavelength around 4 micrometers, then a lead-salt laser, or an optical parametric oscillator (or amplifier) may be used.

Experiments Determining Optimal Wavelength for Laser Use

Various wavelengths from 2 micrometers to 6.45 micrometers were used to stimulate neural tissue. FEL wavelength of 6.45 micrometers was effective and the effect has been reported to be due to the amid II vibrational band of protein (Edwards, et al., *Nature*, 371(6496): 416–419, 1994). While using the wavelength of 6.45 micrometers, nerve stimulation occurred at a pulse energy of 4.5–5.0 mJ/pulse, with a spot size measured to be 0.58 mm. It is note worthy that the volumetric conduction is absent when optical stimulation is used. This is due to the absence of electric potential on the surface of the nerve fiber.

Figure 1:
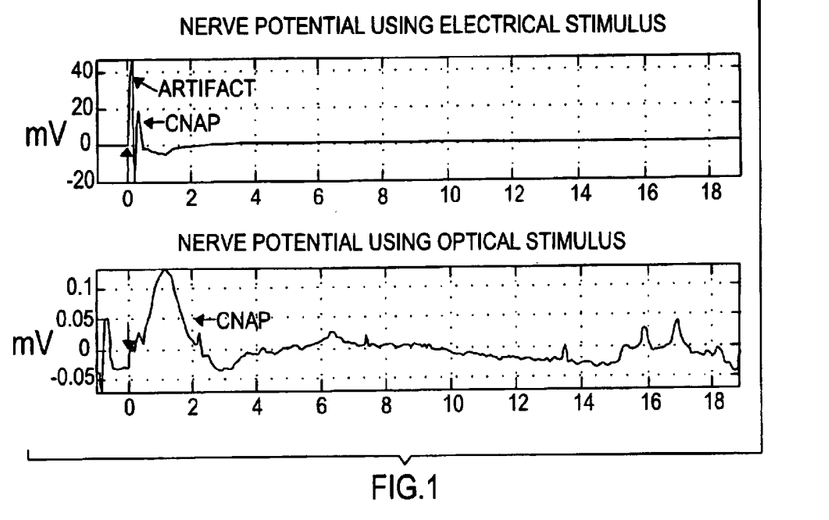
FIG. 1 is a compound nerve action potential (CNAP) recording from optical and electrical stimulus. Optical stimulus was using 6.45 µm FEL laser pulse (4.9 J/cm$^2$). Electrical stimulus was using voltage pulse of 1.0 V and 5 µsec duration. Arrows represent the instant of stimulus.
Figure 2:
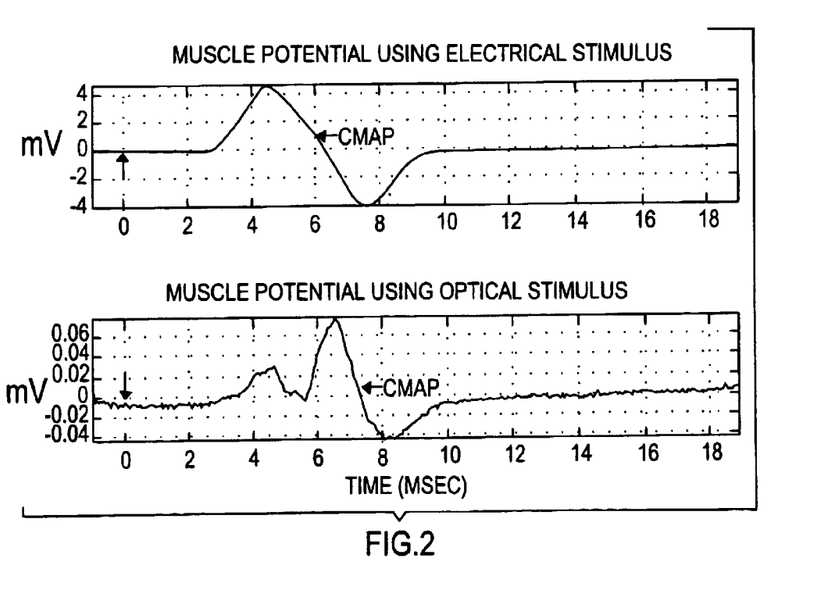
FIG. 2 is a compound muscle action potential (CMAP) recording from optical and electrical stimulus. Optical stimulus was using 6.45 µm FEL laser pulse (4.9 J/cm$^2$). Electrical stimulus was using voltage pulse of 1.0 V and 5 µsec duration. Arrows represent the instant of stimulus.
Figure 3:
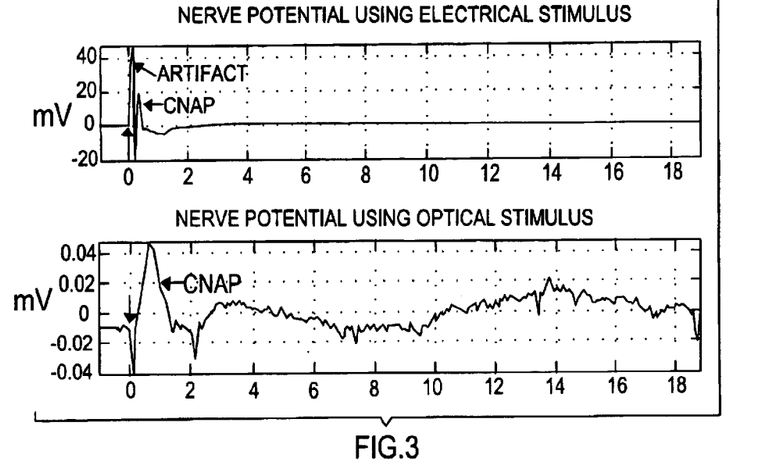
FIG. 3 is a CNAP recording from optical and electrical stimulus. Optical stimulus was using 5.95 µm FEL laser pulse (0.637 J/cm$^2$). Electrical stimulus was using voltage pulse of 1.0 V and 5 µsec duration. Arrows represent the instant of stimulus.
Figure 4:
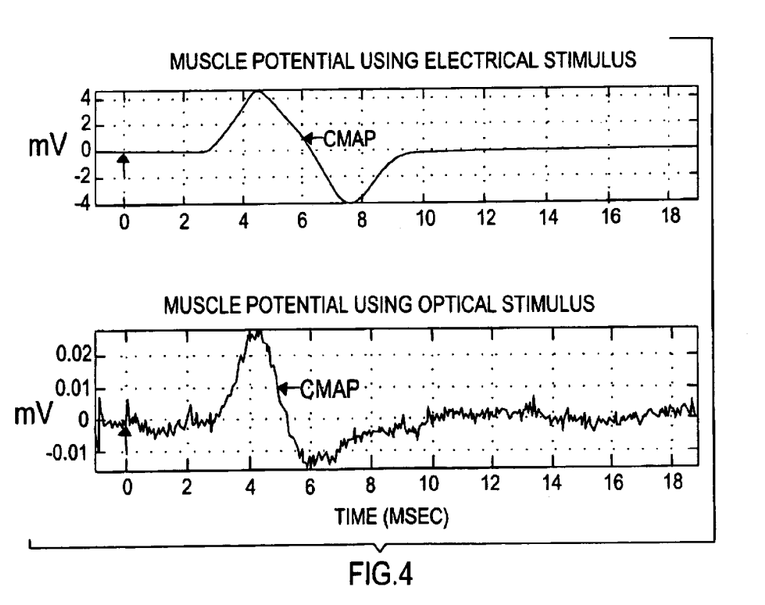
FIG. 4 is a CMAP recording from optical and electrical stimulus. Optical stimulus was using 5.95 µm FEL laser pulse (0.637 J/cm$^2$). Electrical stimulus was using voltage pulse of 1.0 V and 5 µsec duration. Arrows represent the instant of stimulus.
Figure 5:
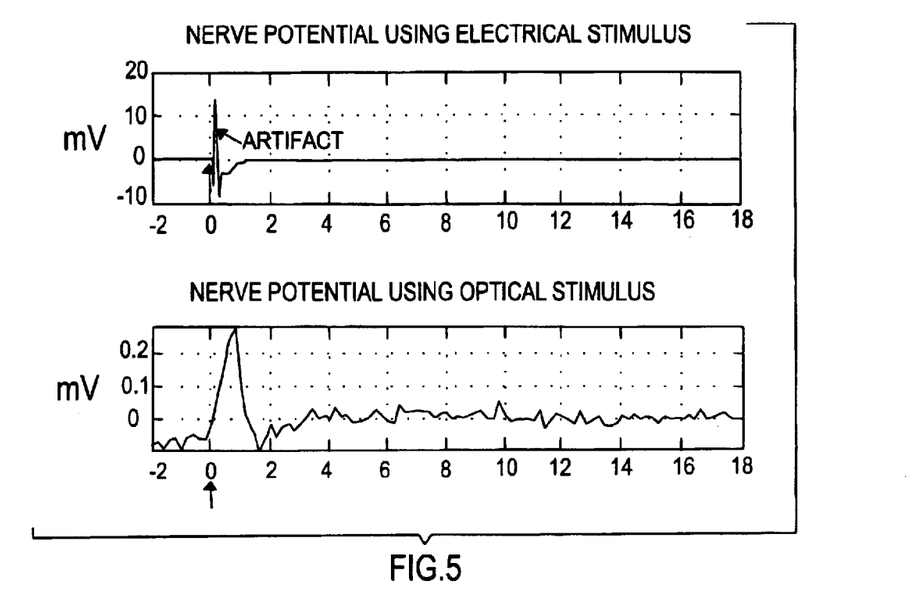
FIG. 5 is a CNAP recording from optical and electrical stimulus. Optical stimulus was using 4.20 µm FEL laser pulse (2.19 J/cm$^2$). Electrical stimulus was using voltage pulse of 0.7 V and 5 µsec duration. Arrows represent the instant of stimulus.
Figure 6:
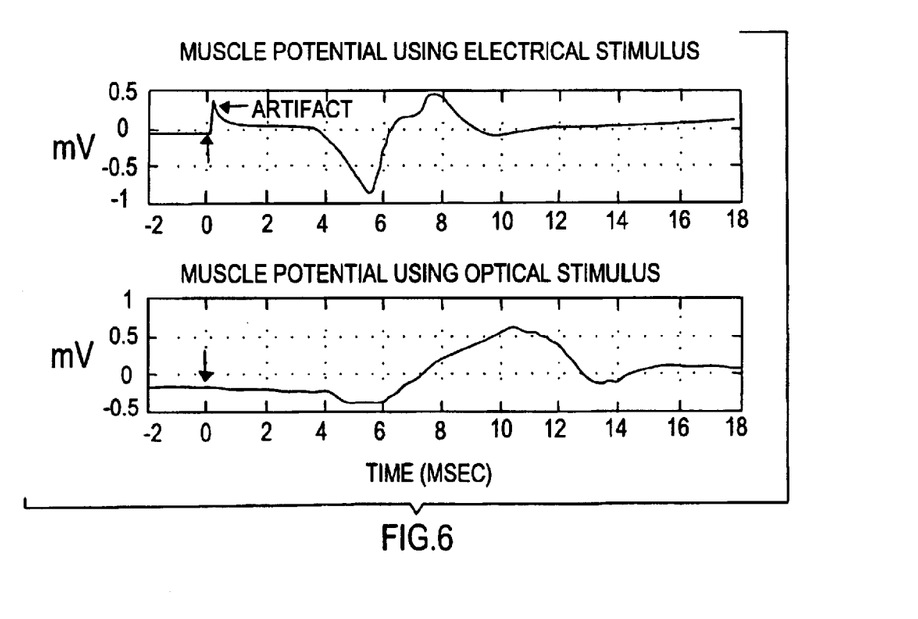
FIG. 6 is a CMAP recording from optical and electrical stimulus. Optical stimulus was using 4.20 µm FEL laser pulse (2.19 J/cm$^2$). Electrical stimulus was using voltage pulse of 0.7 V and 5 µsec duration. Arrows represent the instant of stimulus.

The optical stimulation creates a response demonstrated by a clear peak around 1 msec (FIG. 1, FIG. 2). Optical stimulus was using 6.45 μm FEL laser pulse (4.9 J/cm$^2$). Electrical stimulus was using voltage pulse of 1.0 V and 5 μsec duration. Additional, the muscle potential due to optical stimulation has a peak that occurs at a longer latency and has a longer duration. Optical stimulation at a wavelength of 5.95 micrometers FEL laser pulse (0.637 J/cm$^2$) shows similar characteristics as the above described (FIG. 3, FIG. 4). The optical stimulation response has a lower magnitude compared to electrical stimulus responses. The CNAP and CMAP recordings at a wavelength of 4.2 micrometers FEL laser pulse (2.19 J/cm$^2$) (FIG. 5, FIG. 6) demonstrates the advantage of optical stimulation over electrical stimulation. The artifact, which appears at 0 msec., is absent when optical stimulation occurs.

Figure 7:
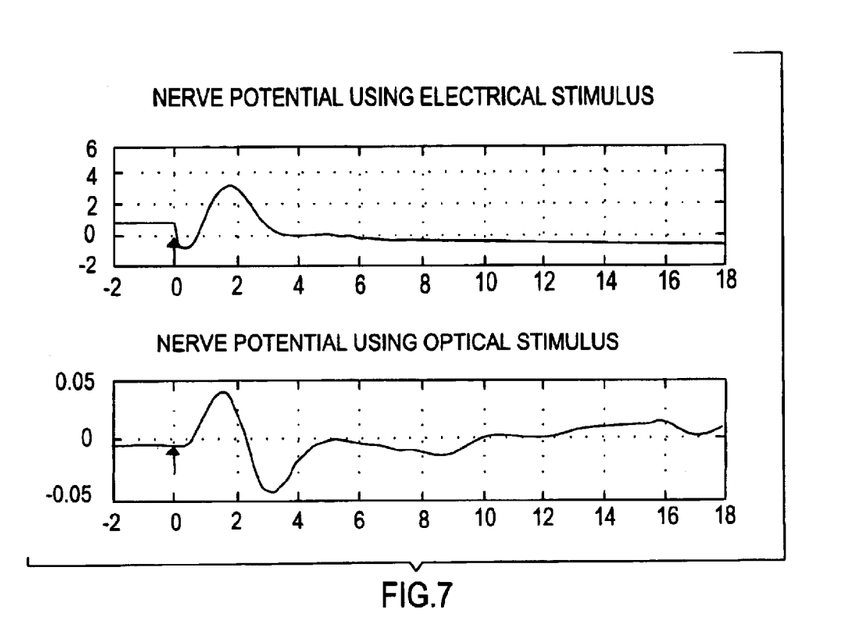
FIG. 7 is a CNAP recording from optical and electrical stimulus. Optical stimulus was using 3.65 µm FEL laser pulse. Electrical stimulus was using voltage pulse of 0.5 V and 1 msec duration. Electrical recordings from the nerve was frequency limited using 300 Hz low pass filter. Arrows represent the instant of stimulus.
Figure 8:
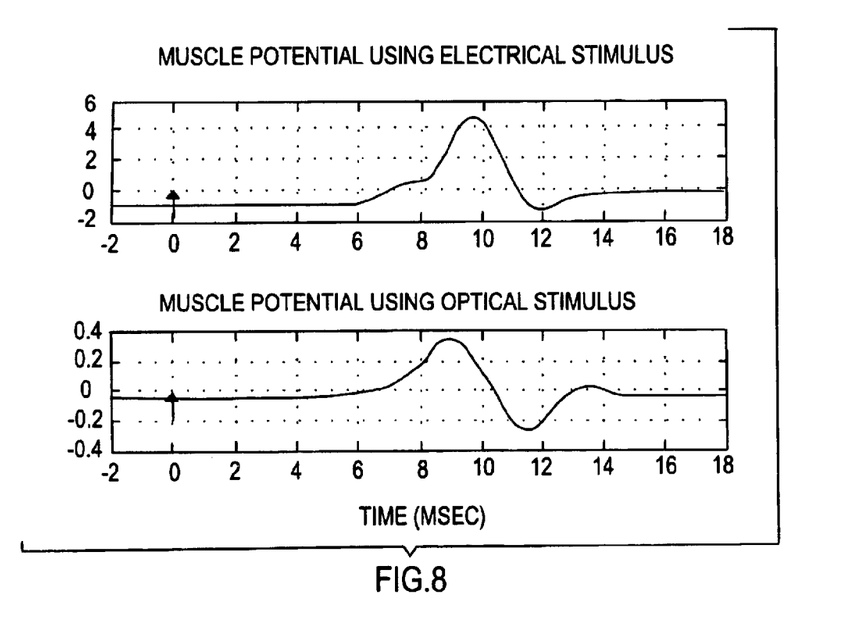
FIG. 8 is a CMAP recording from optical and electrical stimulus. Optical stimulus was using 3.65 µm FEL laser pulse. Electrical stimulus was using voltage pulse of 0.5 V and 1 msec duration. Electrical recordings from the nerve was frequency limited using 300 Hz low pass filter. Arrows represent the instant of stimulus.

Additional wavelengths were tested. Optical stimulation at a wavelength of 3.65 micrometers (FIG. 7, FIG. 8) provided a nerve potential recording that is less in magnitude compared to electrical stimulation.

Optical energy without a wavelength around the water absorption peak, at 2.94 micrometers, was used for optical stimulation. In addition, using wavelengths of 3.1 micrometers and 3.3 micrometers provided a nerve response however, these wavelengths have a greater potential for causing damage to the neural tissues.

Since it is known in the art that biological tissues often follow water absorption characteristics, we expect the same for neural tissue. Thus, by using wavelengths in the range from 3.8 micrometers to 5.5 micrometers, a valley for the water absorption, the unwanted effects of photo-ablation can be minimized. It appears from the optical stimulation that wavelengths around 4 micrometers are more efficient in eliciting nerve response compared to other tested wavelengths. Thus, optical stimulation resulted in a response that had the physiologic behavior of the potential generated by electrical stimulation. Additionally, neuromuscular blockers yielded results that are identical for optical and electrical stimulation. Studies of the wavelengths demonstrate that a wavelength in the range of 3.8 micrometers to 5.5 micrometers produced neural stimulation with minimal nerve ablation.

A study of varying fluences and their effect on the strength or aptitude of the CNAPs induced were investigated. Generally, individual nerve fiber diameters and excitation thresholds varied by small increments, which is normal for this model (Mountcastle, *Medical Physiology*, Volume 1, 1974). This implies that although individual nerve fibers in the nerve bundle obey all or none response to a stimulus, the compound action potential is usually continuously graded. Thus, the CNAP and CMAP represents a population response to stimulation, made up of individual all or none responses from its constituents. When all axons are stimulated there occurs a maximal response, beyond which higher energy stimulation will not elicit a greater response.

Figure 9:
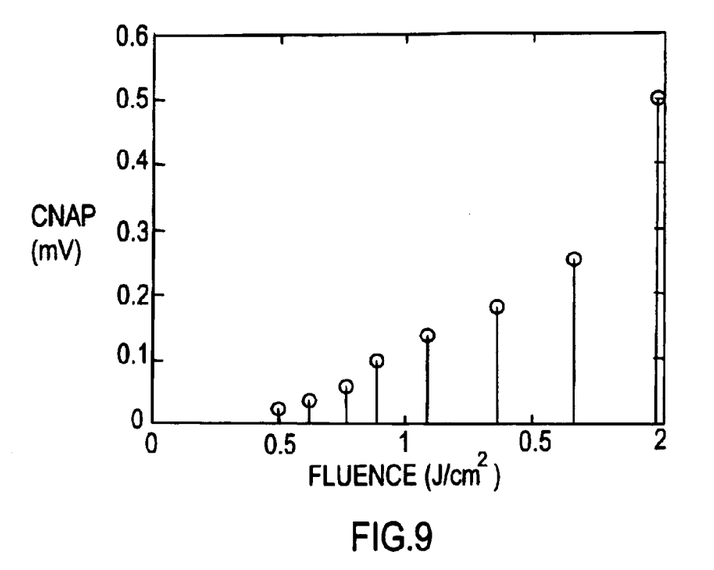
FIG. 9 is a CNAP amplitude with increasing fluence levels for a frog sciatic nerve. Stimulation was using wavelength of 3.8 µm.
Figure 10:
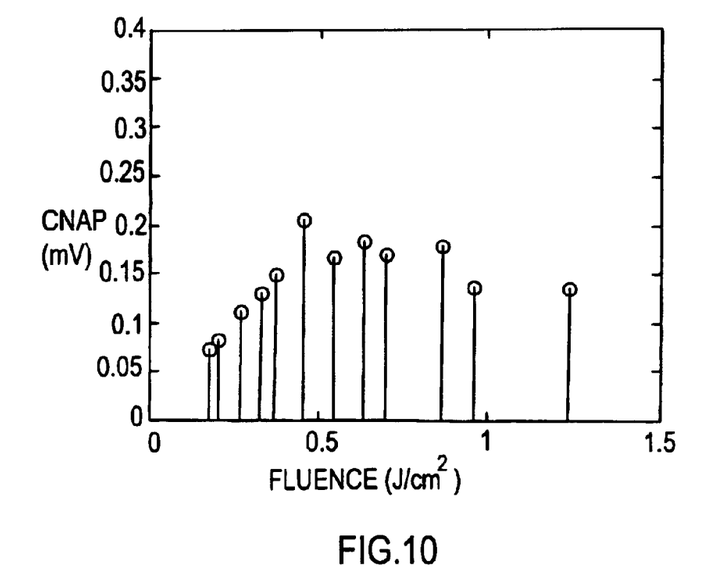
FIG. 10 is a CNAP amplitude with increasing fluence levels for a frog sciatic nerve. Stimulation was using wavelength of 3.9 µm.
Figure 11:
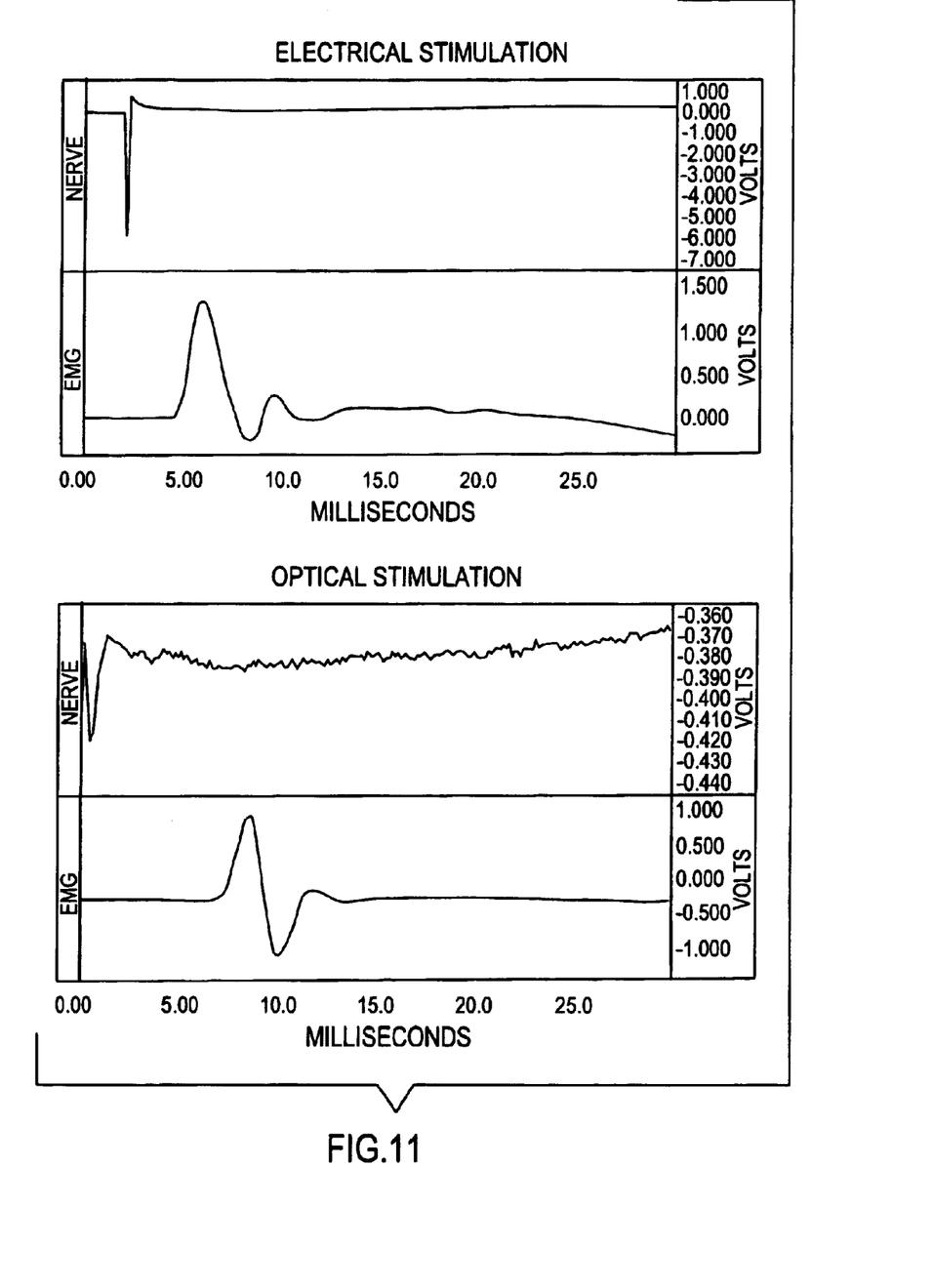
FIG. 11 is a recording of electrical stimulation and optical stimulation of Rat Sciatic Nerve. The electrical stimulation was with an intensity of 1 volt and 5 µs duration. Optical Stimulation of the Rat Sciatic Nerve performed with 4.7 mJ of energy, spot size of 619 microns, wavelength of 4.4 microns, and pulse frequency of 2 Hz using the FEL.
Figure 12:
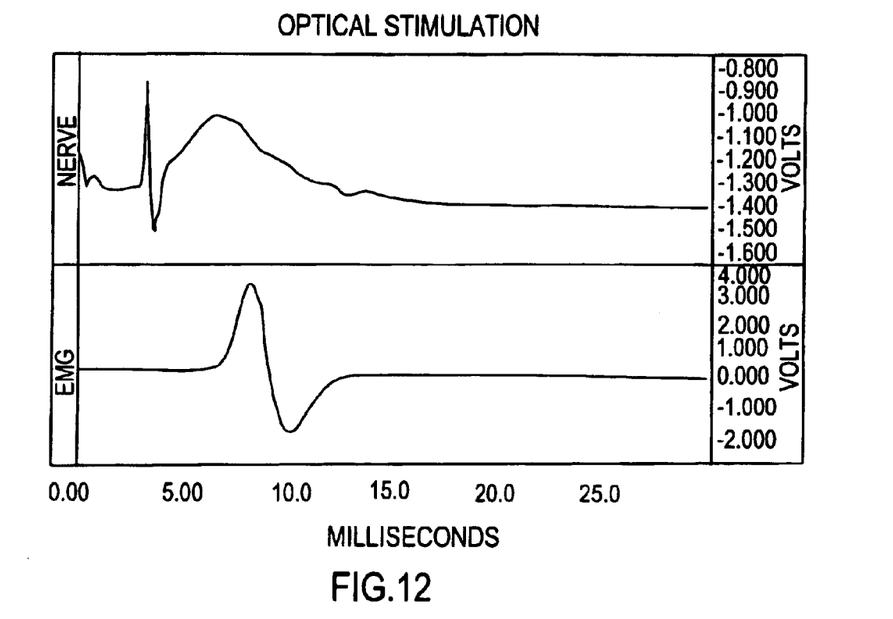
FIG. 12 is a recording of optical stimulation of Rat Sciatic Nerve. Optical Stimulation of Rat Sciatic Nerve with 39 mJ of energy, spot size of 619 microns, wavelength of 4.4 microns, and pulse frequency of 2 Hz using the FEL.
Figure 13:
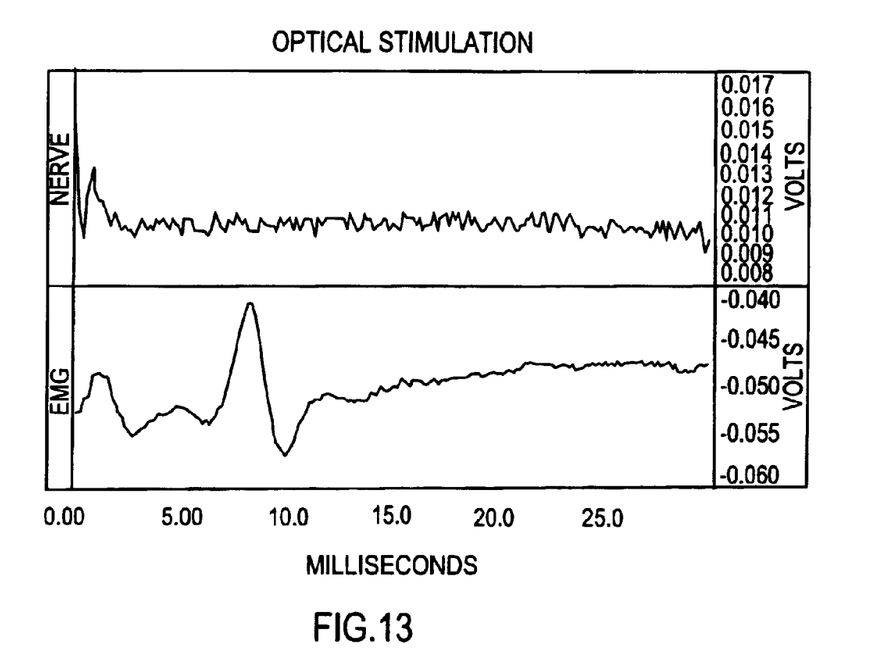
FIG. 13 is a recording of optical Stimulation of Rat Sciatic Nerve with 2.39 mJ of energy, spot size of 619 microns, wavelength of 4.4 microns, and pulse frequency of 2 Hz using the FEL.
Figure 14:
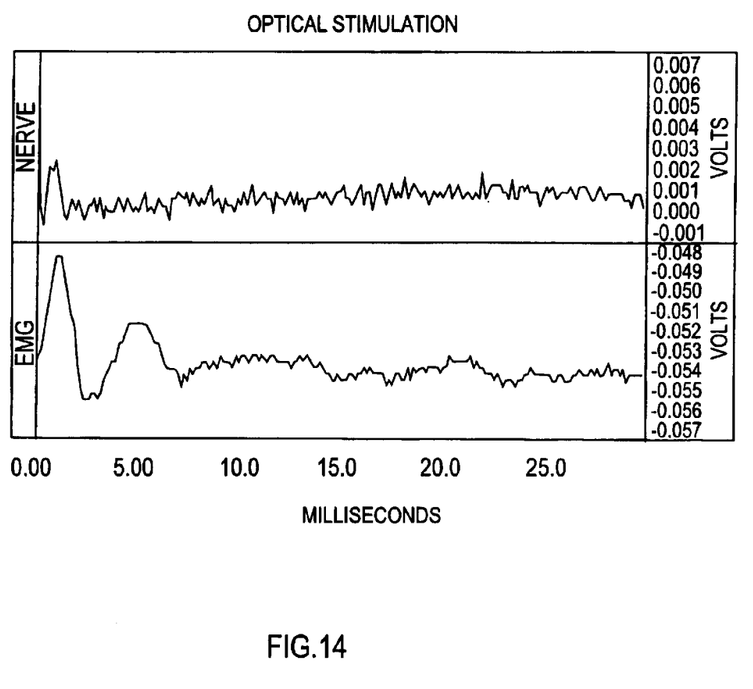
FIG. 14 is a recording of optical Stimulation of Rat Sciatic Nerve with 1.78 mJ of energy, spot size of 619 microns, wavelength of 4.4 microns, and pulse frequency of 2 Hz using the FEL.

The strength of CNAP may vary as due the levels of fluence. The CNAP amplitude for stimulation using 3.8 micrometers as shown in FIG. 9 is observed that the CNAP amplitudes increase linearly with the increase of the fluence at the surface of the nerve. It can be seen that the CNAP response reaches a maximum amplitude at 0.15 mV when fluence becomes greater than 0.4 $J/cm^2$ (FIG. 10).

Methods of Stimulating Neural Tissue

Methods are provided for stimulating neural tissue wherein the source of stimulation is optical energy. In certain embodiments of the method, a free electron laser is used as a source of optical energy. It is possible to use sources other than free electron lasers that are capable of generating the appropriate wavelengths, pulses, and energy levels.

The present invention described herein provides methods of stimulating either neural tissue or nerve fibers with optical energy. In other embodiments, the present invention provides a method of stimulating neural tissue by providing a source capable of generating an optical energy having a wavelength in a range of from 3 micrometers to 6 micrometers at an energy output in a range from 200 microjoules to 5 millijoules, providing a target neural tissue, and focusing the optical energy on the target neural tissue so that the target neural tissue propagates an electrical impulse. A source of optical energy that may be used is a free electron laser. The target neural tissue may be a mammalian nerve, a human nerve, or a sciatic nerve from a leopard frog (*Rana Pepiens*). Focusing the optical energy should occur in an area in a range of 50 micrometers to 600 micrometers. Also, the target neural tissue shall receive the optical energy for an amount of time necessary to provide a stimulation effect. The source, or optical source, may be pulsed. More specifically, when pulsed, each pulse is in a range of from 1 picosecond to 10 picoseconds micropulse and from 1 to 10 microsecond macropulse. The wavelength used is a wavelength which approximately corresponds to a valley for water absorption of a neural tissue. Such valleys of water absorption are in the wavelength ranges of 0.9 micrometers to 2.7 micrometers and 3.8 micrometers to 5.5 micrometers. Additionally, the wavelength used is approximately 4.5 micrometers, approximately 2.2 micrometers, or approximately 1.23 micrometers. In other embodiments, the wavelength is 4.4 micrometers, the energy output is 1.5 mJ, the optical energy occurs in an area of 600 micrometers.

The present invention, herein described, provides a method of stimulating a nerve fiber by providing an optical source capable of generating an optical energy having a wavelength in a range of from 1 micrometers to 8 micrometers at an energy output in a range of 150 microjoules to 5 millijoules, providing the target nerve fiber, and focusing the optical energy on the target nerve fiber so that the target nerve fiber is stimulated. The target nerve fiber can be a mammalian nerve fiber, a human nerve fiber, or a leopard frog (*Rana Pepiens*) sciatic nerve fiber. During focusing, the target nerve fiber receives the optical energy for an amount of time necessary to provide a stimulation effect. The optical source can be pulsed. When the optical source is pulsed, the pulse has a range of from 1 picosecond to 10 picosecond micropulse and from 1 microsecond to 10 microsecond macropulse. Also, focusing of the optical energy occurs in an area in a range of 50 micrometers to 600 micrometers.

In certain embodiments, the present invention provides a method of exciting a nerve comprising: (a) providing a laser to generate a laser beam having a wavelength in a range of from two micrometers to nine micrometers at a power output in a range of from 100 microjoules to 5 millijoules, having an area in a range of 50 micrometers to 600 micrometers, (b) providing a mammalian nerve, (c) focusing the laser beam on the mammalian nerve so that the mammalian nerve conducts a nerve signal. It may be desired to pulse the laser. Although other pulse widths and durations can be used, a pulse can have a range of from 1 picosecond to 10 picosecond micropulse and from 1 microsecond to 10 microsecond macropulse.

Figure 15:
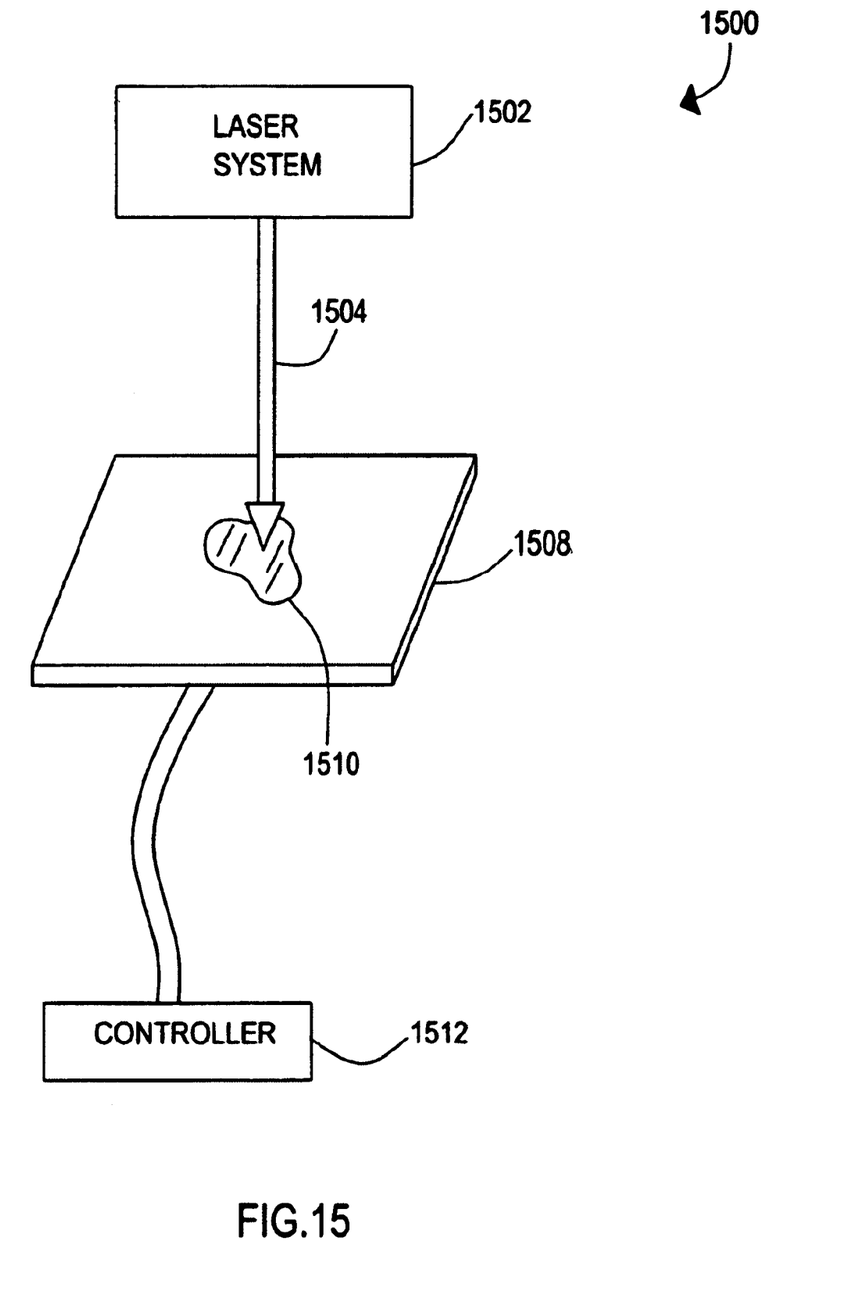
FIG. 15 schematically shows a system for stimulating neural tissue according to one embodiment of the present invention.

The present invention also discloses a system 1500 used for stimulating neural tissue 1510 without damaging the neural tissue, as shown in FIG. 15. More specifically, disclosed herein is a system 1500 that includes an optical source 1502 for gene rating optical energy 1504, a holding plate 1508 for supporting the target neural tissue 1510 to be stimulated by the optical energy 1504, and a means 1512 for recognizing and recording either the CNAP or the CMAP resulting from the optical stimulation. Such means 1512 for recognizing and recording are commercially available. Examples of such means 1512 include the MP100 system previously described, or other systems capable of a similar function. Examples of a holding plate 1508 include, but are not limited to, a dissection pan, a wax bed, a surgical table, or a surgical chair. The holding plate 1508 serves the function of supporting the target neural tissue 1510, whether such neural tissue 1510 is a small tissue sample or a human being.

The present invention discloses a method of stimulating neural tissue by providing an optical source to generate a beam of radiation having a wavelength which approximately corresponds to a valley for water absorption of a neural tissue, providing the neural tissue, and directing the beam of radiation at the neural tissue to be stimulated. Also disclosed is a method stimulating neural tissue by providing a source capable of generating an optical energy having a wavelength in a range of from 0.9 micrometers to six micrometers at a fluence in a range of from 0.07 J/cm² to 25 J/cm², providing a target neural tissue, and focusing the optical energy on the target neural tissue so that action potentials are propagated. During this method, the source may be pulsed. Additionally, the target neural tissue can be mammalian neural tissue, or human neural tissue.

The methods disclosed herein do not damage neural tissue. Neural tissue irradiated at sub-ablative fluence, a wavelength of 4.5 micrometers with a fluence of 0.84 J/cm², was investigated. Upon light microscopy examination of the neural tissue, it was observed that no discernible damage was caused at this fluence. Thus, it can be concluded that at fluence levels of approximately 0.84 J/cm², levels that induce clear CNAP and CMAP potentials in the nerve, there was no thermal damage as observed under light microscopy.

Energy is generally known to have three types of effects on tissue. While photothermal and photochemical effects on neural tissue have been widely studied, the third type of effect, photomechanical, appears to play a minor role with regard to neural tissue. Thus, modifications to the pulse parameters may be used to identify modifications to the photothermal and photochemical responses by the neural tissues.

Since FEL emits continuous laser pulses, an electromechanical shutter is used to select a single pulse from the pulse train. Melles Griot (Irvin, Calif.) electronic shutter is used for gating laser pulses to obtain a single pulse from the pulse train. The shutter controller is triggered using the trigger pulse from the laser.

Gelatin tissue phantoms (70% water) were used to study the amount of temperature increase due to laser irradiation. Temperature measurements were obtained using NI-DAQ hardware and Labview Software from National Instruments (Austin, Tex.). SC2345 module from National Instruments was used as an interface between the DAQ card on the computer and the transducer. T type thermal couple (5TC-TT-T-30–36 from Omega Engineering Inc, Samford, Conn.) was used as a temperature sensor. Factors that determine the amount of temperature increase due to exposure to optical energy include characteristics of the nerve such as absorption, scattering coefficient, thermal conductivity and specific heat (Orr, et al., *Optical-thermal response of laser-irradiated tissue*, Plenum Press, NY, 1995). The temperature increase of the nerve is important since such temperature will have an effect on the nerve. The amplitude of action potentials and conduction velocity in mammalian nerves increases as the temperature increases. However, when the temperature exceeds 44° C., a conduction block results (Davis, et al., *Journal of Neurology, Neurosurgery and Psychiatry*, 39:442–448, 1975). With regard to the neural tissue, a result that has been achieved was that there was not a significant decrease in conduction velocity. A conclusion based upon this result that occurred at least one time could be that a temperature greater than 44° C. was not reached. When the nerve is irradiated at sub-ablative fluence, meaning 4.5 micrometers as a wavelength and a fluence of 0.84 J/sm², it was observed that no discernable damage was present.

The free electron laser used generates pulses of width from 2 microseconds up to 6 microseconds depending upon the operating conditions. Since only thermal confinement and non-stress confinement is guaranteed in the range of the wavelengths of interest, it is possible that stress waves that are generated may propagate from the point of generation. Since axons can be stimulated using mechanical stimulus (Mountcastle, *Medical Physiology*), it can be hypothesized that this can be a possible mechanism behind the exaltation of the nerve. In order to test this theory the sciatic nerve was covered with 2–3 mm of gelatin (95% water) such that any pressure wave propagation through the gelatin will directly effect the nerve underneath. A result that has been achieved is nerve stimulation apparently due to thermal-elastic stress waves. The wavelength of the laser used in such experiment was 4.0 micrometers.

Spot size of the laser beam can be reduced in size. By doing so a small portion of the nerve trunk may be selectively stimulated without disturbing the other axons located on the nerve trunk. By doing so, this is an effective way for an investigator to perform a functional identification of the nerve trunk. More specifically, a researcher would have the ability to map the different portions of the nerve cross section to the specific muscular tissue they innervate. For a clinician, this will serve as a tool to selectively identify the points of damage within a nerve or map subsections of the nerve.

Blocking of Conduction of Nerve Potential

In order to confirm that results obtained within the muscle are due to stimulation of the sciatic nerve, several experiments were performed to block the conduction of the nerve potential. First, the nerve was cut to prevent conduction of the nerve potential to the muscle. Secondly, to observe reversible effects, neuromuscular blockers are used to prevent nerve conduction. Such blocking is expected to result in zero muscle potential. Succinyl Choline is used as a blocker. Succinyl Choline is a cholinergic antagonist and a skeletal muscle relaxant. It acts by depolarizing the nerve cell, thus blocking it from being simulated. In each case the action potential was blocked as expected.

EXAMPLES

Example 1

The Northern Leopard frog (*Rana Pepiens*) is pithed. Subsequent to being pithed, the animal is immobilized on a wax bed. The skin covering the hamstring muscle is cut in order to expose the muscle. Subsequently, an incision is made along the length of the hamstring muscle so as to expose the sciatic nerve. The sciatic nerve is freed from the connective tissue that connected it to the surrounding muscle. For experimental purposes, several pairs of electrodes are placed on the nerve. The first pair of electrodes is capable of electrical stimulation, the second pair of electrodes is capable of recording the nerve potentials, and the third pair of electrodes are pierced into the muscle that the sciatic nerve innervates so that muscle potentials may be recorded. Additionally, the sciatic nerve was kept moist at all times by using saline water. The nerve is initially stimulated electrically to confirm its viability. Electrical recording is performed using the MP100 module. The FEL is used at a wavelength of 4.4 micrometers (pulse width=5 microsecond macropulse, 2 Hz repetition rate) in this experiment. The experimental setup consists of two IR coated plane mirrors that directed the beam from the laser to the target.

What is claimed is:

1. A method of stimulating neural tissue comprising: (a) providing a source for generating an optical energy having a wavelength in a range of from two micrometers to six micrometers at an energy output in a range of from 200 microjoules to 5 millijoules; (b) providing a target neural tissue; (c) focusing the optical energy on the target neural tissue so that the target neural tissue propagates an electrical impulse, wherein the source comprises a tunable laser.

2. The method of claim 1, wherein the source is pulsed, having each pulse in a range of from 1 picosecond to 10 picosecond micropulse and from 1 microsecond to 10 microsecond macropulse.

3. The method of claim 1, wherein the wavelength is approximately 4.5 micrometers.

4. A method of stimulating a nerve fiber comprising: (a) providing an optical source capable of generating an optical energy having a wavelength in a range of from one micrometers to eight micrometers at an energy output in a range of from 150 microjoules to 5 millijoules; (b) providing a target nerve fiber; (c) focusing the optical energy on the target nerve fiber so that action potentials are propagated, wherein the optical source is pulsed, having each pulse in a range of from 1 picosecond to 10 picosecond micropulse and from 1 microsecond to 10 microsecond macropulse.

5. The method of claim 4, wherein the wavelength is approximately 4.5 micrometers.

6. The method of claim 4, wherein the wavelength is approximately 2.2 micrometers.

7. The method of claim 4, wherein the wavelength is approximately 1.23 micrometers.

8. A method of repeatedly exciting a nerve without damaging the nerve, said method comprising: (a) providing a laser to generate a laser beam having a wavelength in a range of from two micrometers to nine micrometers at a power output in a range of from 100 microjoules to 5 millijoules, having an area for stimulation with a diameter in a range of from 50 micrometers to 600 micrometers; (b) providing the nerve; (c) focusing the laser beam on the nerve so that the nerve conducts a nerve signal; (d) repeating step (c), wherein the laser is pulsed.

* * * * *